United States Patent [19]
Gleyak et al.

[11] Patent Number: 6,097,982
[45] Date of Patent: *Aug. 1, 2000

[54] PATIENT-WORN ENERGY DELIVERY APPARATUS

[75] Inventors: John A. Glegyak, Washington County; David J. Peduzzi, Westmoreland County, both of Pa.

[73] Assignee: Lifecor, Inc., Pittsburgh, Pa.

[ * ] Notice: This patent is subject to a terminal disclaimer.

[21] Appl. No.: 09/054,714

[22] Filed: Apr. 3, 1998

Related U.S. Application Data

[63] Continuation of application No. 08/651,274, May 23, 1996, Pat. No. 5,741,306.

[51] Int. Cl.⁷ .................................................. A61N 1/39
[52] U.S. Cl. ............................................................ 607/5
[58] Field of Search .................................... 607/5–8

[56] References Cited

U.S. PATENT DOCUMENTS

| | | |
|---|---|---|
| 3,706,313 | 12/1972 | Milani et al. . |
| 3,886,950 | 6/1975 | Ukkestad et al. . |
| 4,576,170 | 3/1986 | Bradley et al. . |
| 4,619,265 | 10/1986 | Morgan et al. . |
| 4,823,796 | 4/1989 | Benson . |
| 4,928,690 | 5/1990 | Heilman et al. . |
| 5,097,830 | 3/1992 | Eikefjord et al. . |
| 5,405,361 | 4/1995 | Persson . |
| 5,433,737 | 7/1995 | Aimone . |
| 5,470,341 | 11/1995 | Kuehn et al. . |
| 5,601,612 | 2/1997 | Gliner et al. . |
| 5,607,454 | 3/1997 | Cameron et al. . |
| 5,620,470 | 4/1997 | Gliner et al. . |
| 5,721,482 | 2/1998 | Benvegar et al. . |
| 5,741,306 | 4/1998 | Glegyak et al. ............................ 607/5 |
| 5,824,017 | 10/1998 | Sullivan et al. . |

OTHER PUBLICATIONS

"Cardiac Defibrillator Devices", developed by Association for the Advancement of Medical Instrumentation, 1989.

*Primary Examiner*—William E. Kamm
*Attorney, Agent, or Firm*—Buchanan Ingersoll, P.C.

[57] ABSTRACT

A patient-worn energy delivery apparatus for imparting electrical therapy to the body of a patient responsive to an occurrence of a treatable condition. The apparatus includes a voltage converter for converting electrical energy from an initial voltage to a final voltage at a plurality of charging rates, and a defibrillator electrically coupled between the converter and the patient and having an energy reservoir for receiving the electrical energy. The defibrillator produces preshaped electrical pulses such as defibrillation pulses and cardioversion pulses. The apparatus additionally includes an energy delivery controller electrically coupled to the patient and the converter and the defibrillator. The controller causes the converter to provide the electrical energy to the defibrillator at a specific charging rate in response to an energy level in the reservoir. The apparatus may include a plurality of electrodes interposed between the defibrillator and the patient and each electrode preferably has an impedance reducing means contained therein. One embodiment of the apparatus may include a H-bridge to produce a positive-going pulse segment and the negative-going pulse segment within the biphasic exponential signals.

24 Claims, 9 Drawing Sheets

PULSE GENERATOR OUTPUT WAVEFORM

PATIENT-WORN ENERGY DELIVERY APPARATUS

RELATED APPLICATION

This application is a continuation of application Ser. No. 08/651,274, filed May 23, 1996 now U.S. Pat. No. 5,741,306.

BACKGROUND OF THE INVENTION

1. Field of the Invention

This invention relates generally to the treatment of heart defects by the administration of electrical therapy. More particularly, this invention relates to an energy-delivery apparatus for imparting the electrical therapy to the heart.

2. Description of the Related Art

Technology is available for correcting excessively slow heart rates (bradycardia) using implantable devices, commonly referred to as pacemakers, which deliver microjoule electrical pulses to a slowly beating heart in order to speed the heart rate up to an acceptable level. Also, it is well known to deliver high energy shocks (e.g., 180 to 360 joules) via external paddles applied to the chest wall in order to correct excessively fast heart rates, and prevent the possible fatal outcome of ventricular fibrillation or certain ventricular tachycardias. Bradycardia, ventricular fibrillation, and ventricular tachycardia are all electrical malfunctions (arrhythmias) of the heart. Each may lead to death within minutes unless corrected by the appropriate electrical stimulation.

One of the most deadly forms of heart arrythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death may result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment may result in death, implantable pacemakers and defibrillators have significantly improved the ability to treat these otherwise life threatening conditions. Being implanted within the patient, the device continuously monitors the patient's heart for treatable arrhythmias and when such is detected, the device applies corrective electrical pulses directly to the heart.

Normal heart function often can be restored to a person suffering ventricular fibrillation or ventricular tachycardia by a procedure known as cardioversion, the synchronized application of electric therapy to the heart muscle. Pacemakers and defibrillators that apply corrective electrical pulses externally to the patient's chest wall also are used to correct such life-threatening arrhythmias but suffer from a drawback insofar as it may not be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. Alternatively, such patients are kept in a hospital where corrective electrical therapy is generally close at hand. Long term hospitalization, however, is frequently impractical due to its high cost, or due to the need for patients to engage in normal daily activities.

There also are many patients susceptible to heart arrhythmias who are at temporary risk of sudden death. For example, patients who have suffered a myocardial infarction are at substantial risk of tachyarrhythmias for several weeks thereafter. Such patients generally are hospitalized but could be discharged earlier if there were a practical means to protect them from life threatening arrhythmias. Additionally, patients awaiting implantation of an automatic defibrillator may require an external defibrillator to be close at hand, in case they experience a life-threatening tachyarrhythmia. Furthermore, some patients who may benefit from an implantable defibrillator may face an inordinate risk from the surgery required for implanting such a device.

It is evident from the above that there is a need for providing an effective means whereby susceptible patients can receive timely defibrillation or cardioversion without having to undergo an implant procedure and without having to remain hospitalized. Such a device should be capable of determining the energy as it is being delivered to the patient in order to monitor effective treatment, as well as determine that the device is in proper operating condition for delivering these therapeutic energy pulses to the patient.

SUMMARY OF THE INVENTION

The present invention provides for a patient-worn energy delivery apparatus for imparting electrical therapy to the body of a patient responsive to an occurrence of a treatable condition. The apparatus includes a voltage converter for converting electrical energy from an initial voltage to a final voltage. Preferably, the energy is converted at a plurality of charging rates.

The energy delivery apparatus in accordance with the present invention also includes a defibrillator electrically coupled between the converter and the patient and the defibrillator has an energy reservoir for receiving the electrical energy. The defibrillator produces preshaped electrical pulses such as defibrillation pulses and cardioversion pulses. The defibrillator preferably includes at least one insulated gate bipolar transistor for applying the electrical energy to the patient.

The apparatus additionally includes an energy delivery controller electrically coupled to the patient and the converter and the defibrillator. The controller causes the converter to provide the electrical energy to the defibrillator at a specific charging rate in response to an energy level in the reservoir. The plurality of charging rates correspond with a plurality of duty cycles which correspond to a selected output voltage level.

The controller causes the defibrillator to apply a selectable portion of the electrical energy in the form of electrical pulses to the body of the patient in response to the occurrence of the treatable condition. Preferably, the preshaped electrical pulses are approximately exponentially-shaped pulses and may be monophasic or biphasic exponential pulses. The selectable portion is preferably determined by the controller using a minimum energy delivery period and a maximum energy delivery period. The controller measures the voltage and current being delivered to the patient during the pulse delivery period to measure the actual amount of energy being delivered to the patient.

The biphasic exponential pulses preferably have a positive-going pulse segment and a negative-going pulse segment and a selected amount of the electrical energy is applied to the patient during the positive-going pulse segment and a remaining amount of the electrical energy is applied to the patient during the negative-going pulse segment. Preferably, the selected amount of electrical energy is about 60% and the remaining amount of electrical energy is about 40%. Truncation of the positive-going pulse and switching to the negative-going pulse is dependent on the calculated energy being delivered to the patient. The apparatus may include a H-bridge to produce the positive-going pulse segment and the negative-going pulse segment of each of the biphasic exponential signals. Thus, the present invention is controlled by charging the device and measuring the actual energy as it is being delivered to the body of the patient, rather than charging the device to a predetermined higher voltage and interpolating the electrical energy delivered to the patient by measuring the voltage remaining in the defibrillator.

The voltage converter may include an inductive-boost voltage generator having an output voltage level and the energy reservoir may include a plurality of capacitors being adapted to charge substantially in parallel and discharge substantially in series. The inductive-boost voltage generator preferably has a first stage having a first stage output voltage and a second stage having a second stage output voltage and the first stage output voltage is regulated independently of the second stage output voltage. The first stage output voltage may be equal to or less than about 40 volts, and the second stage output voltage may be equal to or less than about 410 volts.

The controller and converter of the apparatus is preferably shut down in response to an overvoltage condition in either the first stage voltage output and second stage voltage output.

The defibrillator may further include a plurality of silicon controller rectifiers and optotriacs and selected ones of the capacitors may be serially connected with other capacitors and respective ones of the silicon controlled rectifiers may be serially interposed between adjacent capacitors. Each of the silicon controlled rectifiers may be controllable with the opto-triacs which cause the silicon controlled rectifiers to conduct responsive to a therapy initiation command from the controller.

The apparatus may additionally include a plurality of electrodes interposed between the defibrillator and the patient and the plurality of electrodes have a conductive surface adapted for placement adjacent the patient's skin and an impedance reducing means contained therein for reducing the impedance between the plurality of electrodes and the patient's skin and the impedance reducing means are activated in response to the occurrence of the treatable condition. Means are provided for measuring the patient trans-thoracic impedance (TTI) to insure proper electrode operation and/or placement.

The apparatus in accordance with the present invention may additionally include a source of electrical energy at a first voltage and a carrier means in the form of an upper body harness or garment to be worn by the patient to hold the plurality of electrodes.

A complete understanding of the invention will be obtained from the following description and the accompanying figures.

DESCRIPTION OF THE EMBODIMENTS

Figure 1:
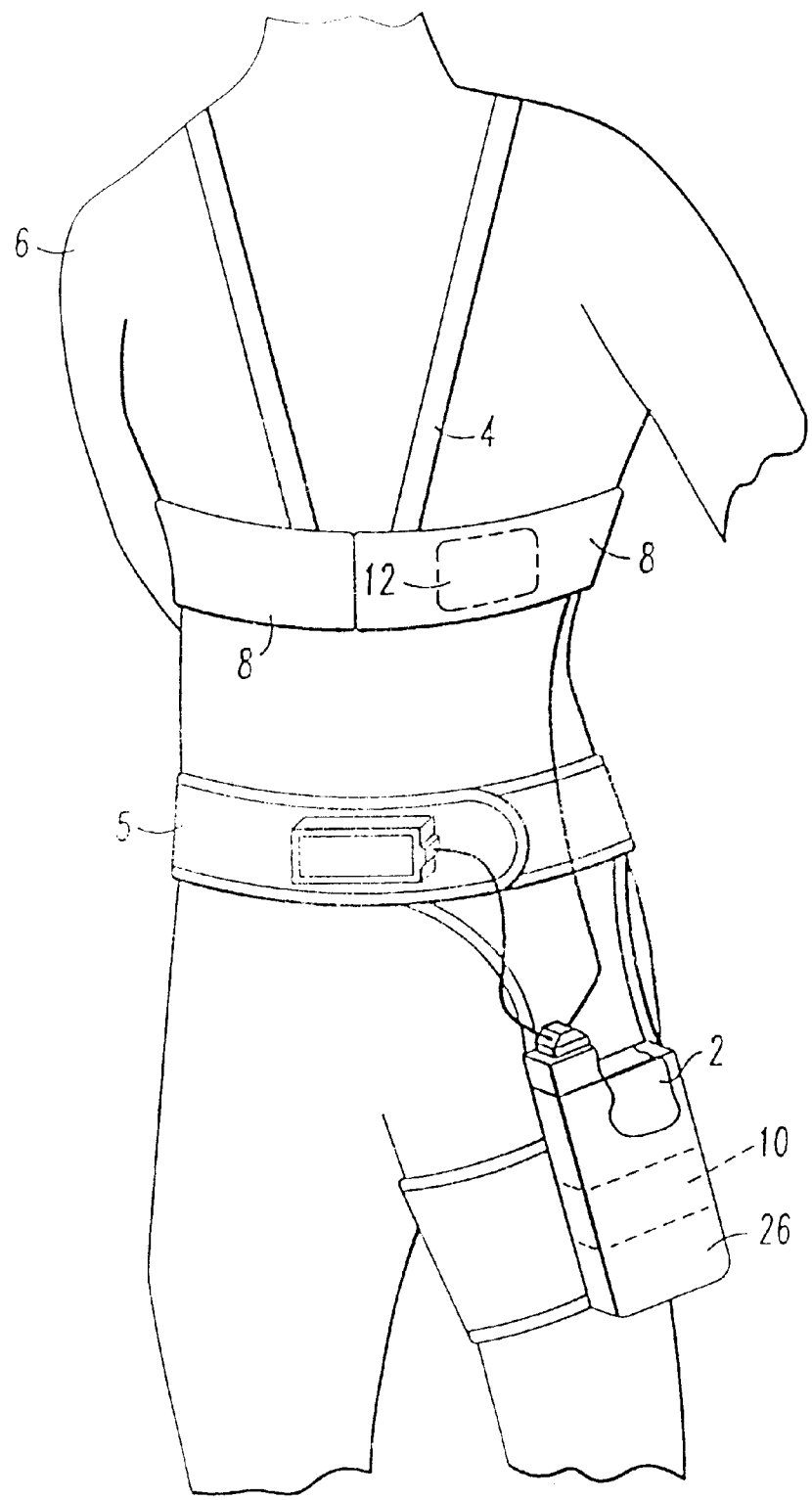
FIG. 1 is an illustration of a patient-worn energy delivery apparatus according to the invention herein.
Figure 2:
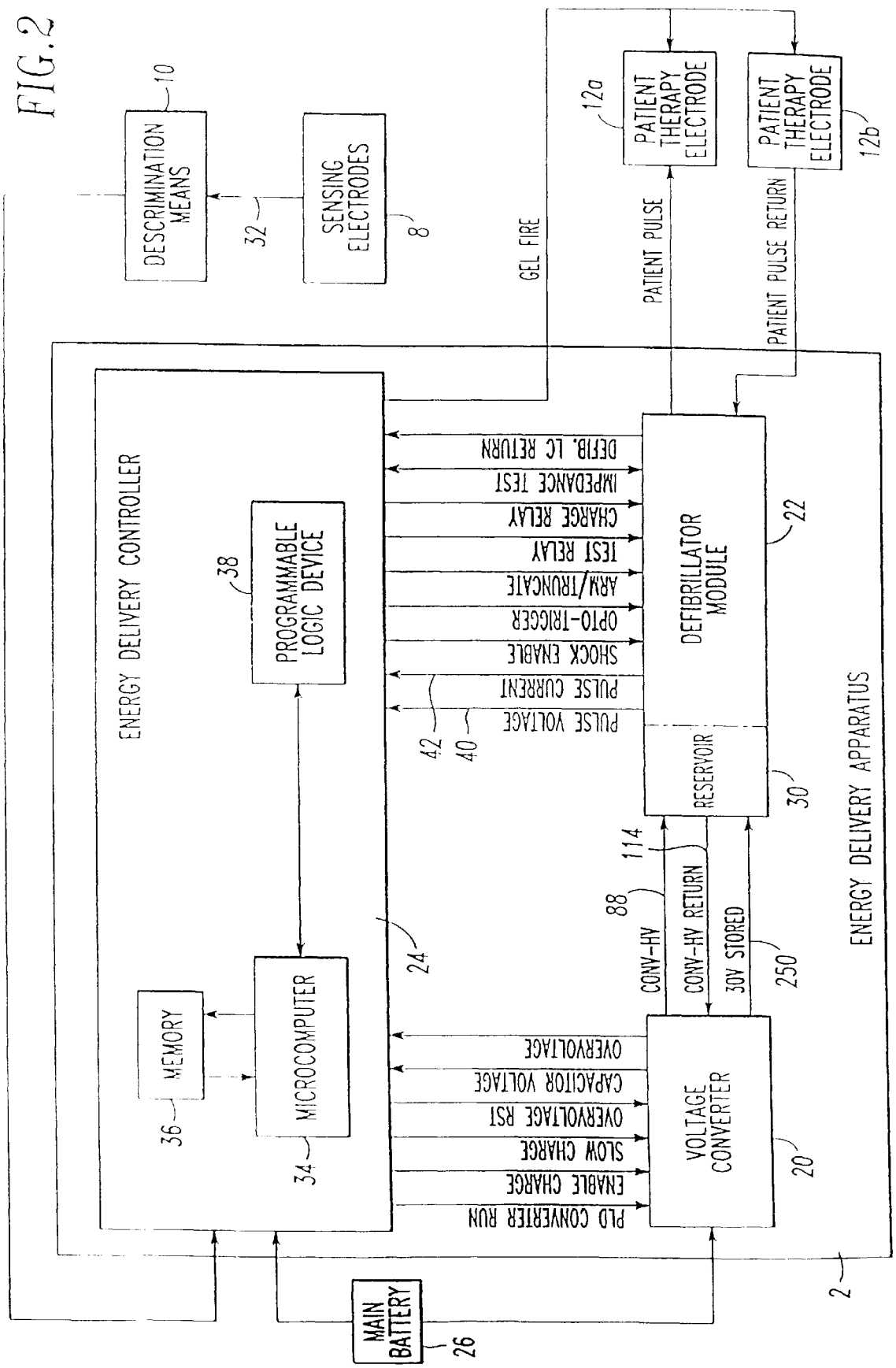
FIG. 2 is a block diagram of one embodiment of the energy delivery apparatus according to the invention herein.

The invention herein provides a patient-worn energy delivery apparatus for imparting electrical energy to the body of the patient in response to the occurrence of a treatable cardiac condition. In FIG. 1, energy delivery apparatus 2 is shown being used in conjunction with carrier means 4 in the form of an upper body harness or garment and a waist-worn holster 5 to be worn by patient 6. Apparatus 2 also can include monitoring means 8, internal to the chest garment, for continuously sensing the patient's heart condition. Signals 32, indicative of the patient's heart condition can be provided by monitoring means 8 to discrimination means 10 for determining the presence of a treatable cardiac condition. When such a condition exists, apparatus 2 can deliver electrical therapy in the form of preprogrammed electrical pulses to patient 6 using, for example, pulse electrodes 12a,12b, preferably located anterior at the apex of the heart and posterior between the shoulders. The pulse electrodes 12a,12b can have an impedance reducing means contained within. The impedance reducing means can be activated by apparatus 2, when the treatable condition is detected, to reduce the impedance between electrodes 12a, 12b and the patient's skin. This impedance may be monitored by the energy delivery apparatus 2 via lines PATIENT IMPEDANCE SENSE—HIGH, PATIENT IMPEDANCE SOURCE—HIGH, and PATIENT IMPEDANCE SENSE—LOW shown in FIG. 5. These lines are collectively referred to as IMPEDANCE TEST which are intermediate the defibrillator module 22 and the energy delivery controller 24 as shown in FIG. 2.

Patient trans-thoracic impedance (TTI) is measured by forcing a small current (typically 1 mA) at a certain frequency (such as about 32 Khz) through the patient by way of the defibrillator pulse electrodes 12a, 12b and measuring the corresponding differential voltage across the electrodes. This low voltage circuitry is protected from the high voltage pulse that is applied to the electrodes during the application of a therapeutic pulse to the patient. This is an improvement over prior art devices which typically incorporate a mechanical relay to provide isolation.

The current is delivered through signal PATIENT IMPEDANCE SOURCE-HIGH, resistor R21 and capacitor C17, PATIENT PULSE (electrodes), PATIENT-PULSE-RETURN (electrode) resistor R23 and capacitor C19 and then to the source circuitry through the system ground. The voltage is monitored at PATIENT IMPEDANCE SENSE-HIGH through capacitor C16 and resistor R20, and PATIENT IMPEDANCE SENSE-LOW through capacitor C18 and resistor R22.

Resistors R2 and R23 are directly in the flow of the forcing current and can't be a high value or the circuits compliance voltage limit will be exceeded. The low value required can not be continuously applied to the high voltage terminals or it would shunt too much current and effect the output pulse and be too large and have other negative effects on the overall circuit. Preferably, high voltage capacitors C17 and C19 are placed in series with the resistors R21 and R23, respectively, to rapidly charge up when the defibrillator pulse is delivered, thereby narrowing the current pulse width through the resistors.

Resistors R20 and R22 are in the measurement path. These resistances can be higher than the source side resistances but are preferably kept relatively low because their variations in values start to effect gain error when combined with the input impedance of the differential measurement circuitry. Thus, capacitors C16 and C18 are added to narrow the current pulse width through the resistors. Again, clamping diodes (not shown) are connected from the signal lines to the supply rails for voltage protection at the measurement circuitry.

An additional reason for sensing patient impedance TTI is to ensure the electrodes are properly in contact with the patient's body to determine the correct operating condition for the energy delivery apparatus. For example, if the sensed patient impedance is abnormally high, this can be an indication that either the electrodes are not in proper body contact or of sensor failure. Conversely, an abnormally low patient impedance measurement may be an indication of a short circuit within the device.

Apparatus 2 can be used in conjunction with the apparatus disclosed in U.S. Pat. No. 4,928,690 and U.S. Pat. No. 5,078,134, both to Heilman et al., which are both assigned to the assignee hereof, and which are both incorporated by reference herein. The apparatus may also include an electrical energy source 26 which can be, for example, a six volt rechargeable battery.

FIG. 2 illustrates one embodiment of energy delivery apparatus 2 according to the invention herein. Apparatus 2 can include voltage converter 20, defibrillator 22, and energy delivery controller 24. Voltage converter 20 can receive electrical energy from battery 26 at an initial voltage and convert the energy using multiple selectable conversion rates to a final voltage. Defibrillator 22 is electrically coupled to converter 20 using energy reservoir 30 for receiving the electrical energy at the final voltage from converter 20. Using the energy stored in reservoir 30, defibrillator 22 produces preprogrammed electrical pulses which can be applied to a patient via, for example, patient therapy electrodes 12a,12b. Defibrillator 22 can provide both defibrillation pulses which are generally asynchronous with respect to the cardiac electrical cycle, and cardioversion pulses, which are generally synchronized with the cardiac cycle. As used herein, "defibrillation" includes both defibrillation and cardioversion. Similarly, apparatus 2 can provide both defibrillation and cardioversion but will be referred to as a "defibrillator."

In general, controller 24 can respond to the occurrence of a treatable cardiac condition as determined by, for example, discrimination means 10, relative to cardiac signals 32 as measured by a plurality of sense electrodes 8. Controller 24 can include microcomputer 34, memory 36, and programmable logic device (PLD) 38.

Microcomputer 34 and memory 36 can monitor voltage converter 20 and defibrillator 22. The electrical therapy pulse energies which are deliverable to the patient can be programmable into memory 36. Microcomputer 34 can measure the pulse voltage 40 across electrodes 12a,12b, and can also read signal 42 which is representative of pulse current, thus implementing real time energy control during electrical therapy pulse delivery. Thus the controller of the present invention measures the actual electrical energy as it is being delivered to the patient during pulse delivery by sensing the pulse voltage and pulse current during the pulse delivering period (i.e., time). Prior art defibrillators merely charge the device to an initial, relatively high voltage and estimate the energy delivered to the patient by measuring the remaining voltage after pulse delivery. Microcomputer 34 additionally can monitor the voltage on reservoir 30 for overvoltage conditions and control pulse truncation during pulse delivery. In addition, microcomputer 34 can send a signal to patient therapy electrodes 12a,12b to activate an impedance reducing means prior to the application of electrical therapy pulses.

The PLD 38 controls the defibrillator 22 based upon inputs from the microcomputer 34. The logic internal to the PLD is implemented to minimize unintended circuit operation. Logic interlocks can be included in PLD 38 to minimize noise, or malfunctions causing premature initiation or termination of charge or discharge operations. PLD 38 also can monitor therapy pulse duration so that the maximum pulse duration period is not exceeded and premature truncation of the electrical pulses is avoided.

Voltage converter 20 can convert the energy available from battery 26 at an initial voltage to a final voltage which can be used to effectively treat an arrhythmic condition. Converter 20 can have an inductive-boost voltage generator, which may be a two-stage voltage generator, that uses duty cycle control of the charging, or conversion rate. A slow charge rate may be enabled at the battery end-of-charge life, thus permitting a therapy pulse to be charged and delivered with low battery energy. Defibrillator 22 can perform the switching operations that permit the energy storage capacitors to be charged in parallel, and to be discharged in series to the patient therapy electrodes 12a,12b. Converter 20 and defibrillator 22 can use a six-volt battery pack capable of a high-rate discharge, such as high-energy-density nickel-cadmium batteries.

Figure 3:
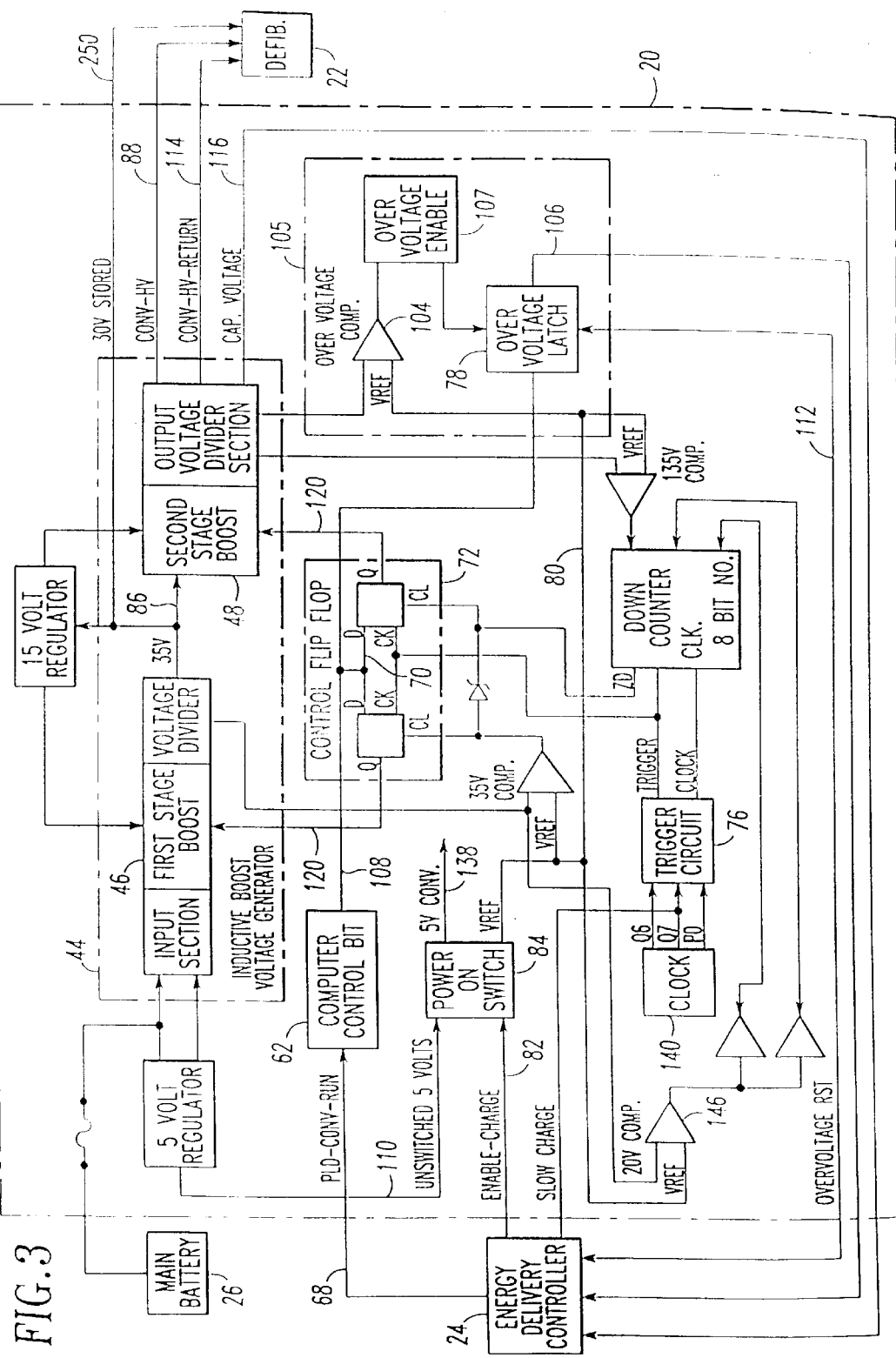
FIG. 3 is a block diagram of a voltage converter according to the invention herein.
Figure 4A:
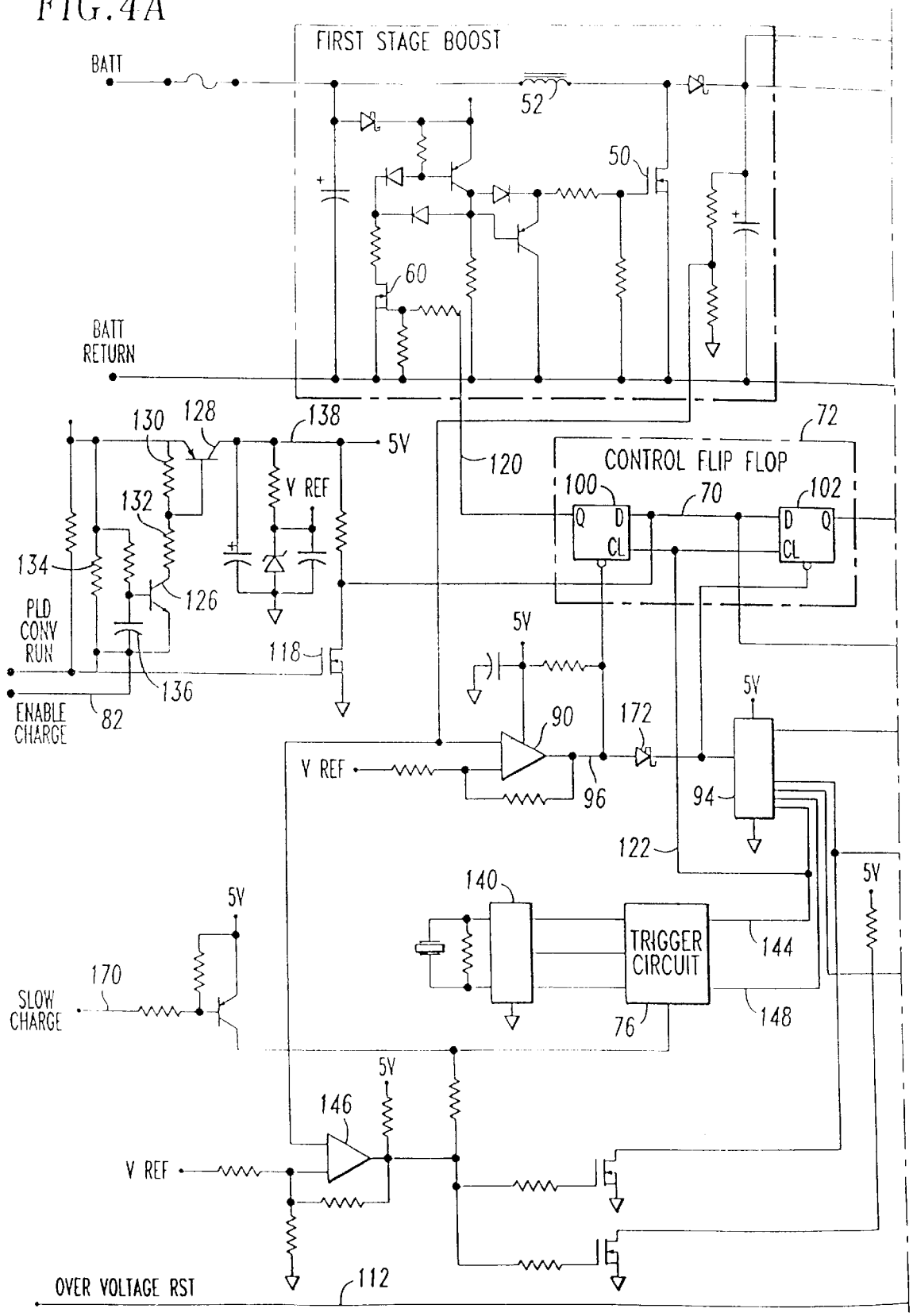
FIG. 4, consisting of FIGS. 4A and 4B, is a schematic diagram of one embodiment of the voltage converter of FIG. 1.
Figure 4B:
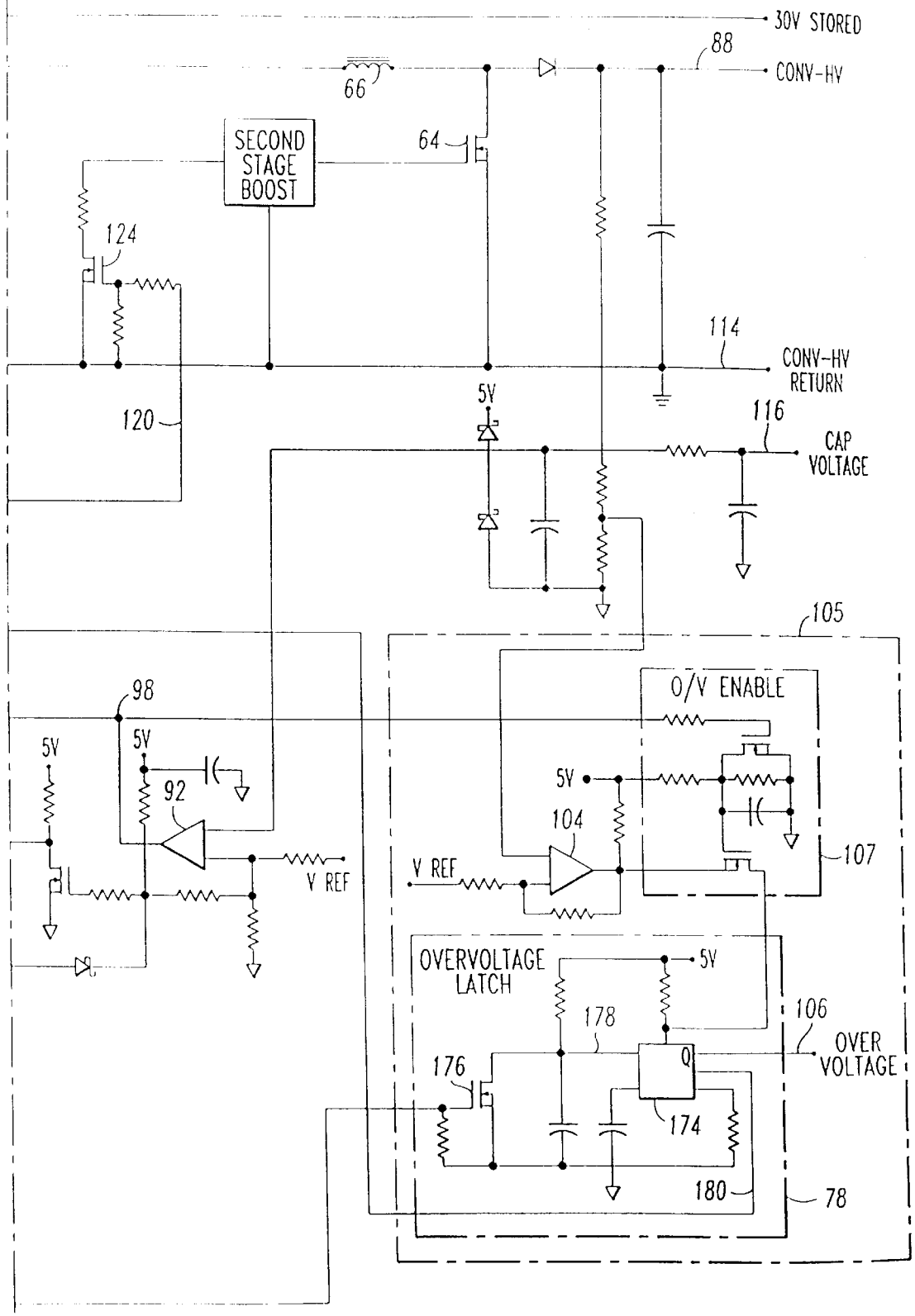

In FIGS. 3 and 4, inductive boost voltage generator 44 converts the energy, received from battery 26, from an initial battery voltage, e.g. about 6 volts DC, to a final voltage suitable for use by defibrillator 22, e.g. about 390V DC. A two-stage inductive-boost voltage generator can be used, although a one-stage boost circuit or configurations using a plurality of stages may also be used. First stage 46 boost generator increases the voltage of the energy input from battery 26, from the initial voltage to an intermediate voltage, for example, about 35V DC. Second stage boost generator 48 then increases this intermediate voltage to the final voltage that will be used by defibrillator 22 to deliver the electrical therapy. For cardioversion, the final voltage value can be any practical voltage desired, typically about 150V DC. For defibrillation, the final voltage value can be about 390V DC. By measuring the actual energy delivered to the patient this voltage can be relatively low since it is not necessary to "over charge" the device to ensure delivery of a proper therapeutic pulse to the patient. Thus the size and number of components used in the device can be minimized for a more comfortable patient-worn external defibrillator. Boost circuits 46, 48 can use power MOSFETs to charge their associated boost inductors. The first stage MOSFET 50 is selected to provide low drain resistance while matching the low-voltage, high-current requirements of this stage. The second-stage MOSFET 64, however, is selected for low-drain resistance at high voltage and low current operation.

Where a one-stage inductive boost voltage generator is used to provide the charging voltage for energy reservoir 30, the generator may use a switching MOSFET having both a high voltage breakdown specification, while simultaneously exhibiting a low drain resistance.

Microcomputer 34 can generate a logic bit to enable the charging of boost circuits 46, 48. Control bit 62 can be received at PLD CONV RUN input 68 and is passed to data input 70 of control flip-flop 72. The MOSFET gate switching circuits of boost circuits 46, 48 can be turned on when the flip-flop 72 is clocked by trigger circuit 76.

The voltage from battery 26 is regulated to about 5 volts, Vref, signal 80, which can be used by overvoltage latch 78. The distribution of Vref, signal 80, is controlled by controller 24 by way of the ENABLE CHARGE signal 82 which activates power switch 84. Controller 24 uses signal 82 to enable a charge of the energy reservoir to occur. However, such charging is inhibited until a bit is clocked in from PLD CONV RUN input signal 68. When a charge command is received on signal 82 from controller 24, output voltage 88 of converter 20 is ramped up to the final voltage selected for the electrical therapy. Ramping can be controlled by varying the duty cycle of the MOSFETs stages 46 and 48 of the inductive boost voltage generator 44. The changing duty cycle controls the turn-on/off time of the switching MOSFETs.

A detailed embodiment of the voltage converter 20 is shown in FIG. 4. In particular, first stage boost MOSFET 50, and second stage boost MOSFET 64, are two such switching MOSFETs. By adjusting the duty cycle of MOSFETs 50, 64 it is possible to avoid uncontrolled ratcheting of the current of the first stage boost inductor 52, and second stage boost inductor, 66. Trigger circuit 76 can be used to generate multiple rates to change the total time of the duty cycle during voltage ramp-up.

The duty cycle can be dependent on the level of first stage output voltage 86 and second stage 48 output voltage 88. Control flip-flop 72 can decode three discrete conditions of the output level. When the first stage 46 boost output voltage 86 is less than about 20 volts, the on time for MOSFET 50 is set for a duty cycle of approximately 9 percent which remains in force until output voltage 86 reaches about 20 volts. This short duty cycle is desired to provide the capacitor bank with a controlled, smoothly-increasing charge voltage to limit charging current peaks, thus providing an initially gradual turn-on and smooth start-up.

When voltage 86 is equal to or greater than about 20 volts, and second stage 48 boost output voltage 88 is under about 135 volts, the duty cycle is increased by the trigger circuit 76 to about 42 percent. This significant increase in duty cycle shortens the inductor discharge time, allowing a faster build-up of second stage 48 boost output voltage 88. In this manner, voltage 88 approaches its final value more rapidly than during initial start-up.

When the second stage 48 boost voltage 88 is equal to or greater than about 135 volts, trigger circuit 76 increases the MOSFET duty cycle to about 69 percent, allowing a maximum build-up rate of second stage 48 boost output voltage 88 to, for example, 390 volts. Voltage outputs 86, 88 can be monitored using first stage boost voltage comparator 90, and second stage boost comparator 92, respectively. Outputs 96, 98 from comparators 90, 92 can be decoded by a down-counter 94 as a binary value. Counter 94 down-counts from this value to clear control flip-flop 72, turning off MOSFETs 50, 64 and allowing inductors 52, 66, respectively, to discharge. When a subsequent trigger pulse is received by counter 94 from trigger circuit 76, counter 94 again counts down from a particular decoded count so that the charge-discharge cycle is repeated. Control flip-flop 72 can consist of two D-type flip-flops 100, 102 each being associated with a particular boost stage 46, 48. First stage flip-flop 100 can be reset independently of second stage flip-flop 102 when the first stage 46 output voltage 86 exceeds about 35 volts. This can permit the first stage output 86 to regulate at about 35 volts without constantly resetting second stage output 88. This independence is desirable because, otherwise, second stage boost circuit 48 may discharge each time first stage boost circuit 46 resets to regulate output 86 to about 35 volts. This discharging action could increase the time for output 88 to achieve the desired voltage level.

First stage 46 output voltage 86 can be protected from exceeding 35 volts by turning off MOSFET 50 when output voltage 86 exceeds about 35 volts, thus terminating the charging of inductor 52. In general, inductor 52 is not charged until output voltage 86 drops below about 35 volts when MOSFET 50 is turned on. Second stage 48 boost output voltage 88 also can be monitored for overvoltage when charging the capacitor bank and defibrillator 22.

When overvoltage comparator 104 senses that output voltage 88 is in the range of about 391 to about 402 volts DC, comparator 104 sets overvoltage latch 78. Latch 78, in turn, alerts controller 24 to the overvoltage condition by signal 106. Also latch 78 disables control bit 62, data bit 108 at control flip-flop 72, thus rendering boost circuits 46, 48 inoperative on the next pulse from trigger circuit 76. Latch 78 can stay set so long as unswitched 5 volt supply 110 is present and overvoltage reset line 112 from controller 24 is not activated.

Typically, controller 24 can discharge energy reservoir 30 when the latch 78 is set. In this embodiment, latch 78 can only be reset by removing battery 26, or by activation of signal 112 by controller 24. Therefore, converter 20 can be shut down independently of controller 24 in the event of an overvoltage condition on output 88. The nominal operating value for voltage 88 from converter 20 is typically between about 150 and about 390 volts.

The voltage across output terminals 88, 114 of converter 20 can be continuously monitored by controller 24 from initial startup to a fully-charged energy reservoir state. For this monitoring, a scaled voltage can be provided on CAP VOLTAGE signal 116. Voltage converter 20 can use control signals, namely PLD CONV RUN input 68 and ENABLE CHARGE signal 82, both of which can be active low signals. When PLD CONV RUN signal 68 is low, MOSFET 118 turns off and a logic high bit is applied to the data input 70 of controller flip-flop 72. This bit is clocked to the Q output 120 on the positive-going edge of trigger pulse 122 at a CLK input of each of flip-flops 100, 102, and is used to turn on MOSFETs 60 and 124 for charging the first and second stage boost inductors 52, 66, respectively. In the absence of the PLD CONV RUN data bit, inductors 52, 66 will not charge.

When ENABLE CHARGE signal 82 is low, transistor 126 is turned on, and the base of transistor 128 is forward-biased by resistors 130, 132. Resistor 134 and capacitor 136 provide a small delay in turning on transistor 126. This delay is desirable to provide time for the defibrillator charge relay 220 to close before converter 20 is turned on. A similar delay for relay turn-off can be generated by the PLD 38. After the specified delay time, transistor 128 passes the unswitched five volts to the circuits five-volt CONV LINE 138.

When the first stage 46 inductive-boost voltage generator is activated, the first stage MOSFET 50 is turned on and permits first stage boost inductor 52 to charge from battery 26.

Clock 140 generates a crystal-controlled frequency that can be used by the trigger circuit 76 and down counter 94 to control converter 20 to produce a slow initial build-up voltage followed by a more rapid build-up as output voltage 88 approaches the desired level. The basic clock frequency can be used to clock down counter 94. The resultant divided frequencies can then be used by trigger circuit 76 to clock control flip-flop 72 and enter the count for the down counter 94. The firing rate of trigger circuit 76 can be selected by 20-volt comparator 146. When output 86 of first stage boost circuit 46 is less than about 20 volts, trigger circuit 76 can produce pulses at a first frequency F1 144 (F1 may be approximately 40 kHz). When the output voltage 86 is generally equal to or greater than about 20 volts, trigger circuit 76 produces a second frequency F2 148 which may about twice that of F1 (F2 may be approximately 80 kHz). Twenty-volt comparator 146 and 135-volt comparator 92 can change the binary count at counter 94. The output of comparator 92 also may be used to inhibit over voltage latch 78 when the voltage is less than 135 volts. Typically, trigger circuit 76 can load the preset count into down counter 94. The preset count can be decoded from the 20 and 135 volt comparators 146, 92, respectively, at the preset inputs of counter 94. Along with the loading of the count, trigger pulse clocks the data bit at flip-flops 100, 102 to their Q outputs. Counter 94 begins to count down from the preset count upon a low-to-high transition of the clock.

When the Q outputs of dual flip-flop 72 are set, boost circuits 46, 48 can charge their inductors 52, 66, respectively. When the Q outputs are cleared, inductors 52, 66, may be discharged. The D inputs 70 of flip-flop 72 are wire-ORed with the overvoltage latch 78 to shut down boost generators 46, 48 whenever output 88 of second stage boost generator 48 is in an over-voltage state. Under this condition, inputs 70 into flip-flop 72 are set low and the two Q outputs are set low on the next trigger circuit pulse.

SLOW CHARGE input 170 is available to converter 20 permitting converter 20 to operate at a substantially constant rate, thus reducing the required input current and increasing the battery run time. This permits charging and delivery of a therapy pulse to the patient as the battery nears the end of its charge. Comparator 90 resets flip-flop 100 whenever the first stage boost voltage 86 reaches about 35 volts. Flip-flop 100 is held in a reset state until voltage 86 drops slightly below about 35 volts, as determined by hysteresis which is implemented in comparator 90. By these means, the first stage 46 boost is regulated to about 35 volts. Diode 172 prevents the comparator output 96 from resetting second stage flip-flop 102, but allows counter 94 to clear both flip-flops 100, 102.

Overvoltage detector 105 can include overvoltage latch 78, overvoltage comparator 104 and overvoltage enable module 107. Overvoltage latch 78 can include timer 174 and reset transistor 176. When an overvoltage condition is detected in second stage boost output 88, a logic low is generated on the OVERVOLTAGE line 106. If converter 20 is in the start-up mode, the output of 135 volt comparator 92 is logic high, because the second stage 48 boost typically is not in an overvoltage condition at this point. Thus, during start-up, and up to an output voltage of 135 volts, the overvoltage latch is not activated. Timer 174 can be configured as a latch with its Q output 106 normally high. This Q state can be changed by applying a logic low through signal 178 to reset device 174, which remains latched with its Q output set low. It is preferred that the latch state be removed by disconnecting the battery pack or the energy delivery controller 24 activating the OVERVOLTAGE RESET LINE 112. A low logic level on line 112 represents an overvoltage condition at output 88 of boost generator 48. Discharge output 180 of timer 174 can be used to set the input 70 of flip-flops 100, 102 to logic low to disable boost circuits 46, 48.

Figure 5:
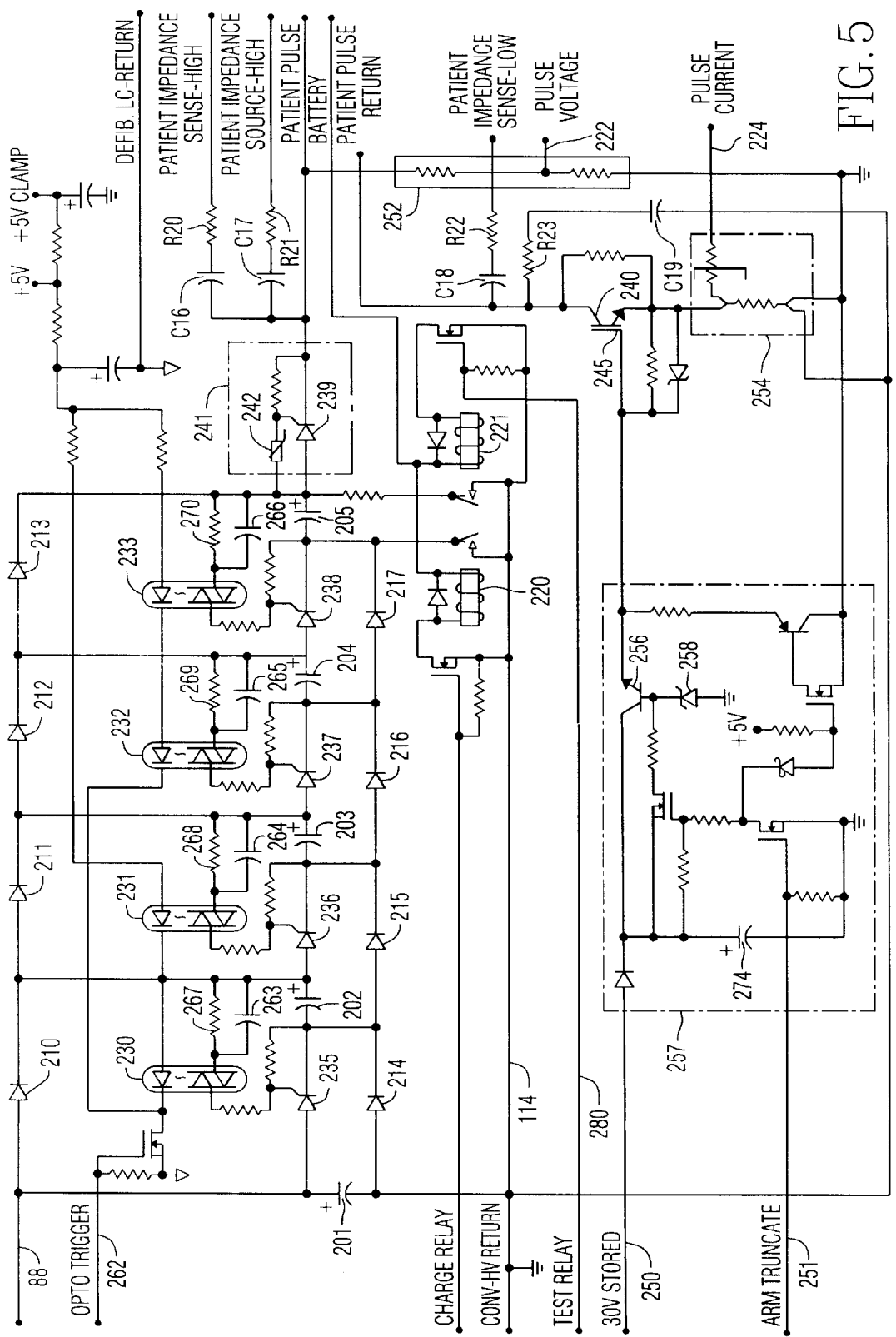
FIG. 5 is one embodiment of a monophasic defibrillator according to the invention herein.

One embodiment of the defibrillator 22 in FIGS. 2 and 3 is described in the context of FIG. 5. In general, the energy reservoir can be a capacitor bank which includes capacitors 201 through 205, each of which can be an 800 microfarad capacitor. It is preferred to charge the capacitor bank 201–205 in parallel and to switch 201–205 to a serial connection for therapy pulse delivery to a patient. The amount of energy stored on the parallel connected capacitors 201–205 is determined by the parameters stored in the controller memory 36. The maximum available stored energy can be determined by the level of the boost voltage 88 from the converter which is, in turn, controlled by an energy delivery controller, such as controller 24 in FIGS. 2 and 3. The delivered energy is continuously monitored by controller 24 using scaled voltage and current inputs developed by defibrillator 22. The energy delivered to the patient is also controlled by controller 24 independent of the pre-pulse inter-electrode impedance. The controller 24 accomplishes this task by truncating the width of the applied pulse at the appropriate time to supply the desired energy. Controller 24 considers substantially all circuit losses in calculating the delivered energy. Residual energy remaining in the capacitor bank 201–205, post-truncation, is not automatically removed. This energy, along with additional charging input from the converter, may be utilized for a subsequent therapy pulse during a given treatment sequence, should one becomes necessary. Optionally, residual charge remaining on the capacitor bank 201–205 after delivery of a therapy pulse may be removed by activating the test relay 221.

Controller 24 can be programmed to provide periodic maintenance charge-discharge cycles to "form" capacitors 201–205 in the energy storage bank during periods of device non-use.

When the ENABLE CHARGE signal 82 is asserted, thereby initiating a charge cycle, the charge relay 220 closes before the application of boost voltage from the converter, which occurs when the PLD CONV RUN input 68 is asserted. The capacitor bank 201–205 can allow an effective maximum energy storage of about 300 joules at 390 volts or a minimum of 35 joules at 132 volts. The higher energies can be used for unsynchronized defibrillation and the lower energies can be used for synchronized cardioversion.

The parallel charging path for capacitor bank 201–205 is through a series-parallel diode arrangement using diodes 210–217, and charge relay 220. This diode arrangement can allow sharing of both current and voltage to minimize electrical strength on the components. During capacitor bank charging, opto-triacs 230–233 remain inactive, holding the discharge silicon controlled rectifiers (SCRs) 235–239 in the off or quiescent state. It is preferred that first capacitor 201 is not switched so as to provide a load for voltage converter output voltage. After capacitors 201–205 reach their desired charge level, an insulated gate bipolar transistor, (IGBT) 240 can be armed in preparation for delivering a therapy pulse to the patient. Capacitors 201–205 then can be switched into a series configuration to multiply the boost voltage to greater than about 650 volts, with a maximum multiplication to 1950 volts. Metal oxide varistor, (MOV), 242 or charge holding circuit 241 can present a high series resistance to capacitor discharge until the multiplied voltage of capacitors 201–205 surpasses the MOV 242 firing level.

IGBT 240 is enabled by first turning on the gate before the parallel-to-series switching of the capacitor bank 201–205 occurs. In this state, IGBT 240 is armed and waiting for the controller to initiate the shock pulse. Prior to receiving the shock pulse, IGBT 240 is not conducting high currents even though gate 245 is biased on. This is because the drain resistance in MOV circuit 241 is high, and capacitor bank 201–205 is still parallel-connected.

When controller 24 initiates a shock pulse via the OPTO TRIGGER line 262, capacitor bank 201–205 is switched to a series-connected state through silicon controlled rectifiers (SCRs) 235–239 and MOV circuit 241 is turned on by the rapidly rising voltage across capacitor bank 201–205. Typically, IGBT 240 turns on three to five times faster than SCRs 235–239. This places IGBT 240 well into conduction before MOV circuit 241 impedance drops sufficiently to allow maximum discharge current. Under this condition, the maximum drain-to-source voltage is below the breakdown voltage for IGBT 240.

The MOV circuit 241 can be used to allow the stored charge in capacitor bank 201–205 to reach a high potential before use as a shock pulse. The MOV circuit 241 isolates the patient from the remaining circuitry during charging of the capacitors.

IGBT gate 245 obtains its voltage from the first stage 46 boost voltage generator by way of 30V STORED line 250. This voltage can be regulated to the desired 20 volts by the gate drive circuit 257. As the bias is applied to gate 245, IGBT 240 is armed and ready to conduct the shock pulse. Controller 24 can command the truncation of the shock pulse to control the therapy pulse energy content by measuring the voltage and current being applied to the patient over time, when controller 24 asserts the ARM TRUNCATE signal 251 to perform pulse truncation. When signal 251 is low, IGBT 240 is turned on to deliver the therapy pulse. When signal 251 goes logic high, IGBT 240 is turned off. This turns off or truncates the shock pulse.

Controller 24 can be programmed to monitor the pulse voltage so that IGBT 240 is turned off when the voltage is lower than the breakdown voltage of IGBT 240, thereby avoiding device damage. Controller 24 can measure the energy of the applied pulse essentially in real time by monitoring the pulse voltage 222 and pulse current 224 levels. These measurements are made by using a precision voltage divider 252 and a precision current sense resistor using Kelvin contacts 254 to compensate for contact induced potentials. Controller 24 can use the measured quantities to calculate actual delivered energy by sensing the voltage and current delivered by the device to the patient and the truncation time for the shock pulse. Also from these parameters, abnormal conditions may be detected in order to terminate the shock pulse in an orderly manner. It is preferred that the shock pulse not be truncated when pulse voltage 222 is greater than the breakdown voltage of IGBT 240. This condition is monitored by controller 24 with input from precision voltage divider 252. In addition to prematurely truncated therapy pulses, an excessively long shock pulse can be prevented using the logic of PLD 38 (FIG. 2) and a comparator, as well as controller 24, each of which can be made to immediately turn off IGBT 240 to truncate the pulse if the duration exceeds a specified time.

If an overvoltage condition should occur, converter 20 can shut down and controller 24 can command defibrillator 22 to close test relay 221 thus removing the charge from capacitor bank 201–205. During pulse delivery, each opto-triac 230–233 can be triggered momentarily when the OPTO TRIGGER signal is present. When OPTO TRIGGER signal 262 is sent, capacitors 201–205 are connected in series by SCRs 235–239 which are, in turn, each driven by a respective opto-triac. The emitters of opto-triacs 230–233 can be driven simultaneously by the logic of PLD 38, (FIG. 2). Complete switching of capacitor bank 201–205 from the parallel configuration to the series configuration typically takes place in 200 microseconds or less.

Opto-triacs (230–233) are used to trigger the reconfiguration of the energy storage capacitors (201–205) from a parallel combination to a series combination by turning on SCRs 235–238. It is desired that this triggering current be stopped before the desired truncation of the outgoing defibrillation pulse. Once the opto-triacs are turned on they can't be turned off by a control signal. Each stage opto-triac—SCR combination uses a "forward" energy storage capacitor as its trigger supply. After the opto-triacs are turned on, capacitors 263–266 will eventually charge up to the voltage of the storage capacitor, thereby stopping current flow through the opto-triacs and turning them off. Resistors 267–270 remove charge from the cornunutation capacitor so that the next defibrillator pulse can be triggered.

One sequence of control signals from the initial charging to discharging of energy reservoir 30 can be as follows:

1. ENABLE CHARGE signal 82 becomes logic low which closes charge relay 220 before the application of the boost voltage to energy reservoir 30.

2. The PLD CONV RUN signal 68 drops to logic low which initiates the charging of energy reservoir 30 to a level precalculated by controller 24.

3. PLD CONV RUN signal 68 goes logic high which removes the boost charging voltage from energy reservoir 30.

4. The ENABLE CHARGE signal goes logic high which opens charge relay 220.

5. Both ENABLE SHOCK signal 270 and ARM TRUNCATE signal 251 drop to active logic low. Signals 270, 251 are independently-generated computer control signals which enable the application of the voltage across capacitor 274 to gate 245 of IGBT 240, thus arming IGBT 240 for a subsequent therapy pulse application. The stored boost voltage can be regulated to about 20 volts by transistor 256 and diode 258.

6. OPTO TRIGGER signal 262 momentarily becomes logic high which triggers opto-triacs 230–233 to discharge capacitors using a serial connection. Signal 262 can be fixed at about 300 microseconds by a one-shot circuit. The therapy pulse can then be delivered through the patient, in series with IGBT 240.

7. ARM TRUNCATE signal 251 becomes logic high which turns off IGBT 240, providing a high-impedance path to the therapy shock pulse, or truncating it thus removing the pulse from the patient.

8. TEST LOAD signal 280 becomes logic high, which closes test relay 221 and removes residual charge from capacitors 201–205.

MOV circuit 241 can be designed to hold the series charge across capacitors 201–205 up to about 650 volts. As each of the SCRs 235–239 fires, the voltage across circuit 241 increases until device 242 conducts thus turning on SCR 239. Because the firing voltage is higher than the clamping voltage of MOV circuit 241, SCR 239 conducts and capacitors 201–205 discharge until truncated by the action of IGBT 240.

Typically, the electrical therapy pulses delivered to a patient are sinusoidal or trapezoidal in shape. However, the invention herein can provide electrical therapy pulses which have generally exponential waveforms. Such waveforms can be a monophasic exponential pulse as illustrated by waveform 300 in FIG. 6a. A biphasic exponential pulse train also can be provided, as seen in waveform 302 in FIG. 6b.

Figure 6:
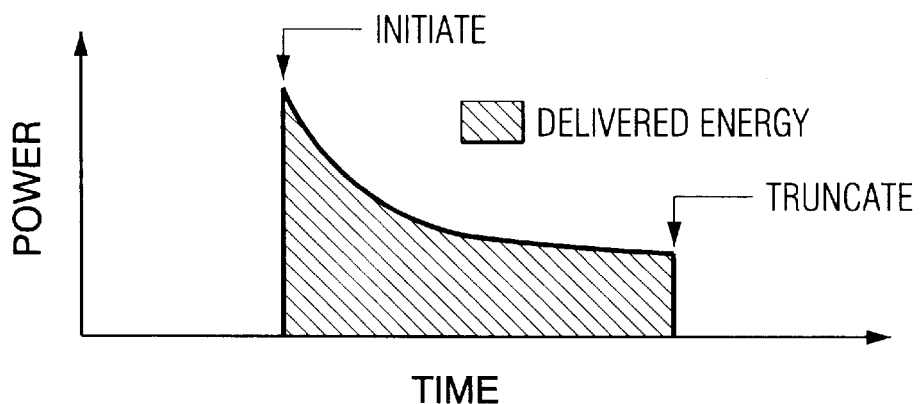
FIG. 6, consisting of FIGS. 6A and 6B, 6a and 6b show waveform diagrams for monophasic and biphasic defibrillator pulses, respectively, according to the invention herein.

A truncated exponential biphasic waveform such as waveform 302 in FIG. 6b can reduce the energy needed to perform efficient defibrillation inasmuch as biphasic waveforms have a lower defibrillation threshold than monophasic waveforms for defibrillation of humans. Energy reductions of up to 60% have been shown in some clinical studies through the use of biphasic waveforms. Further, studies have also shown that biphasic waveforms provide an increased success rate over monophasic waveforms for the initial shock for conversion of induced ventricular arrhythmias.

The monophasic waveform 300 may be applied for approximately 8 milliseconds. The positive-going pulse segment 304 and the negative-going pulse segment 306 may each be applied for 4 milliseconds. Preferably, there is a transition period or off time of approximately 100 microseconds between each positive-going pulse segment 304 and each negative-going pulse segment 306 where no energy is delivered to the patient. As shown in FIG. 6b, about 60% of the total pulse energy typically is delivered during the positive-going pulse segment 304 of the exponential pulse, with the remaining 40% being delivered during the negative-going pulse segment 306.

Controller 24 in FIG. 2 may be programmed to allow either polarity to be used for the first phase of the pulse. Also, the percentage of the total energy delivered in each phase of the pulse can also be programmable. Multi-phasic embodiments may also be implemented. A truncated exponential waveform can be preferred over a damped sinusoid because the bulky inductors usually associated with a sinusoidal pulse delivery can be eliminated. Also, less energy may be required for successful defibrillation or cardioversion. This increased efficiency permits the use of smaller components with lower power dissipation thus providing a cardioverter/defibrillator that weighs less and is smaller than similarly functioning devices. Indeed, the weight and size reductions are such that the cardioverter/defibrillator according to the invention herein can be comfortably worn by the patient using a light weight upper body garment, supplying support for the sensing and therapy electrodes, and a waist belt with integral holster for the cardioverter/defibrillator.

Figure 7A:
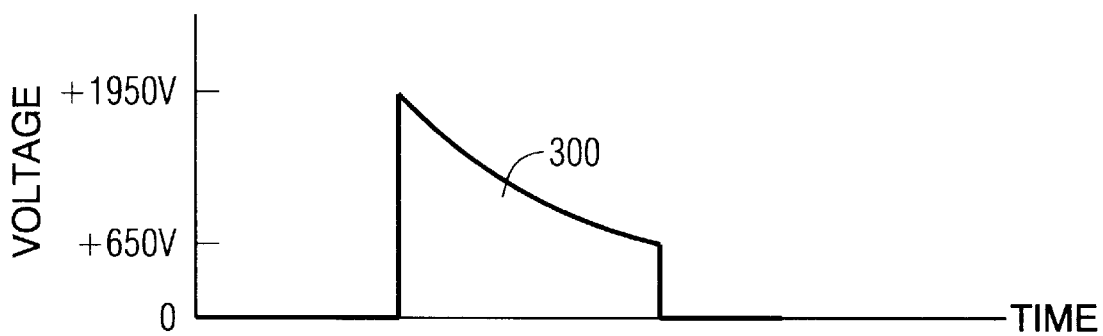
FIG. 7 is one embodiment of a biphasic defibrillator according to the invention herein.
Figure 7B:
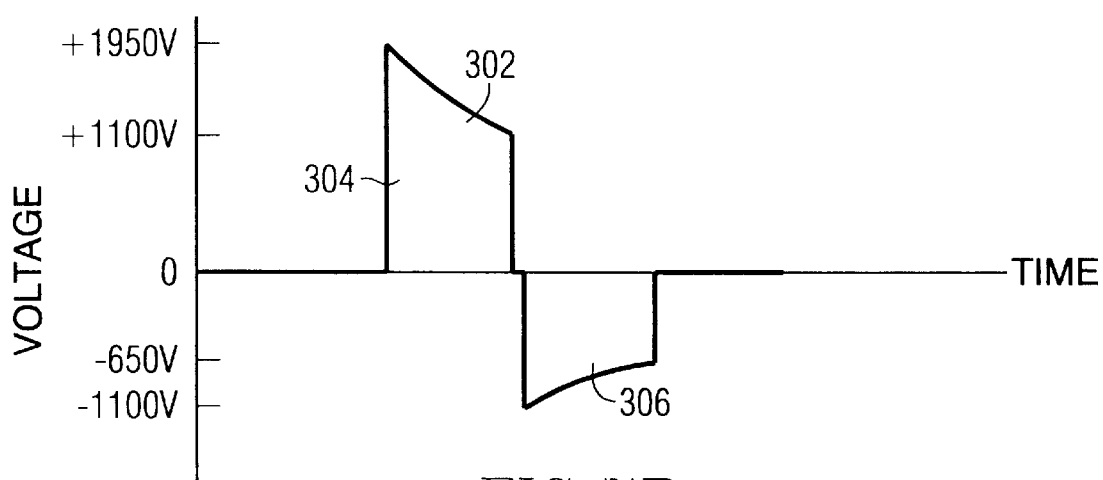
Figure 8:
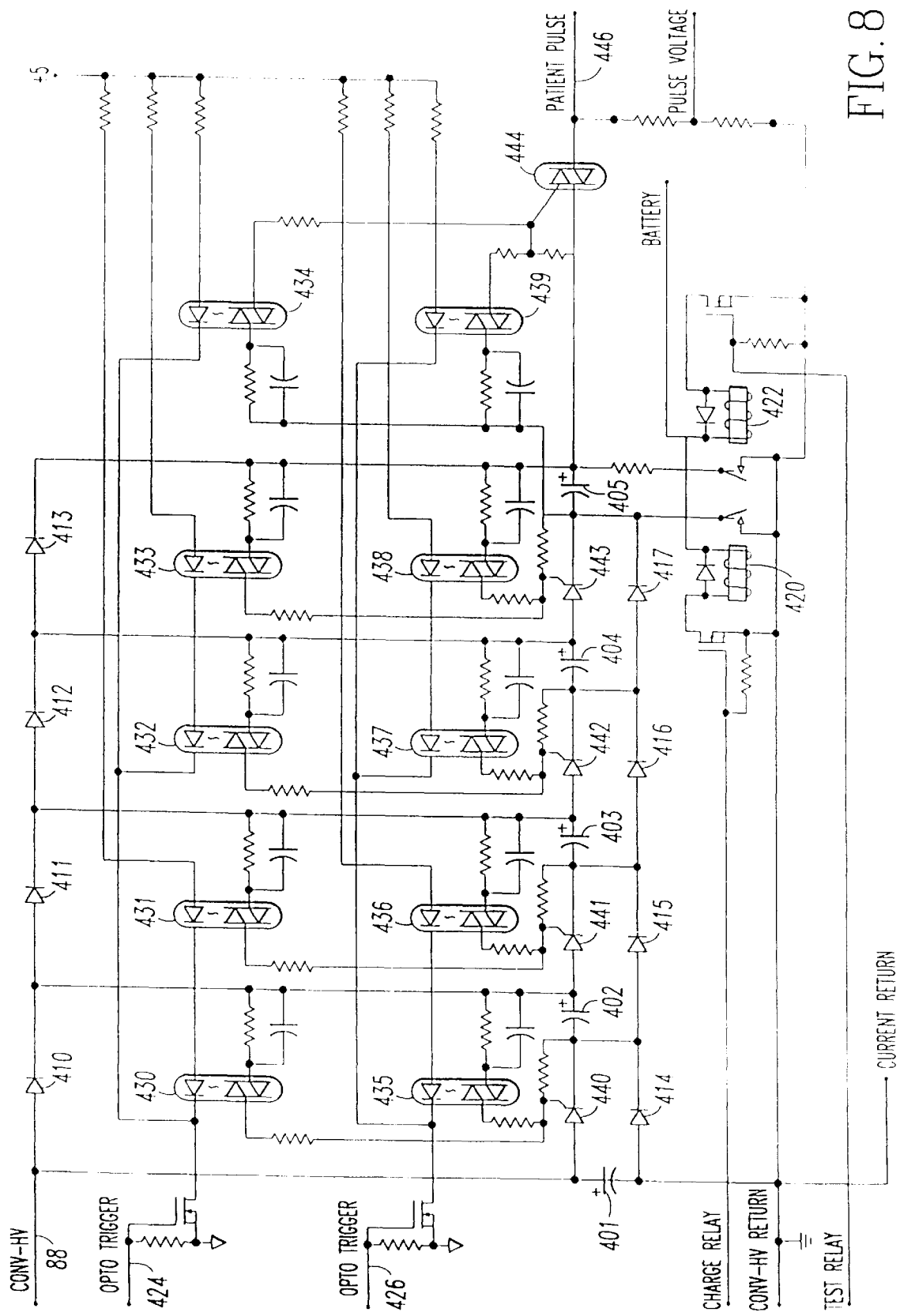
FIG. 8 is the polarity-reversing H-bridge of the biphasic defibrillator shown in FIG. 7.
Figure 9:
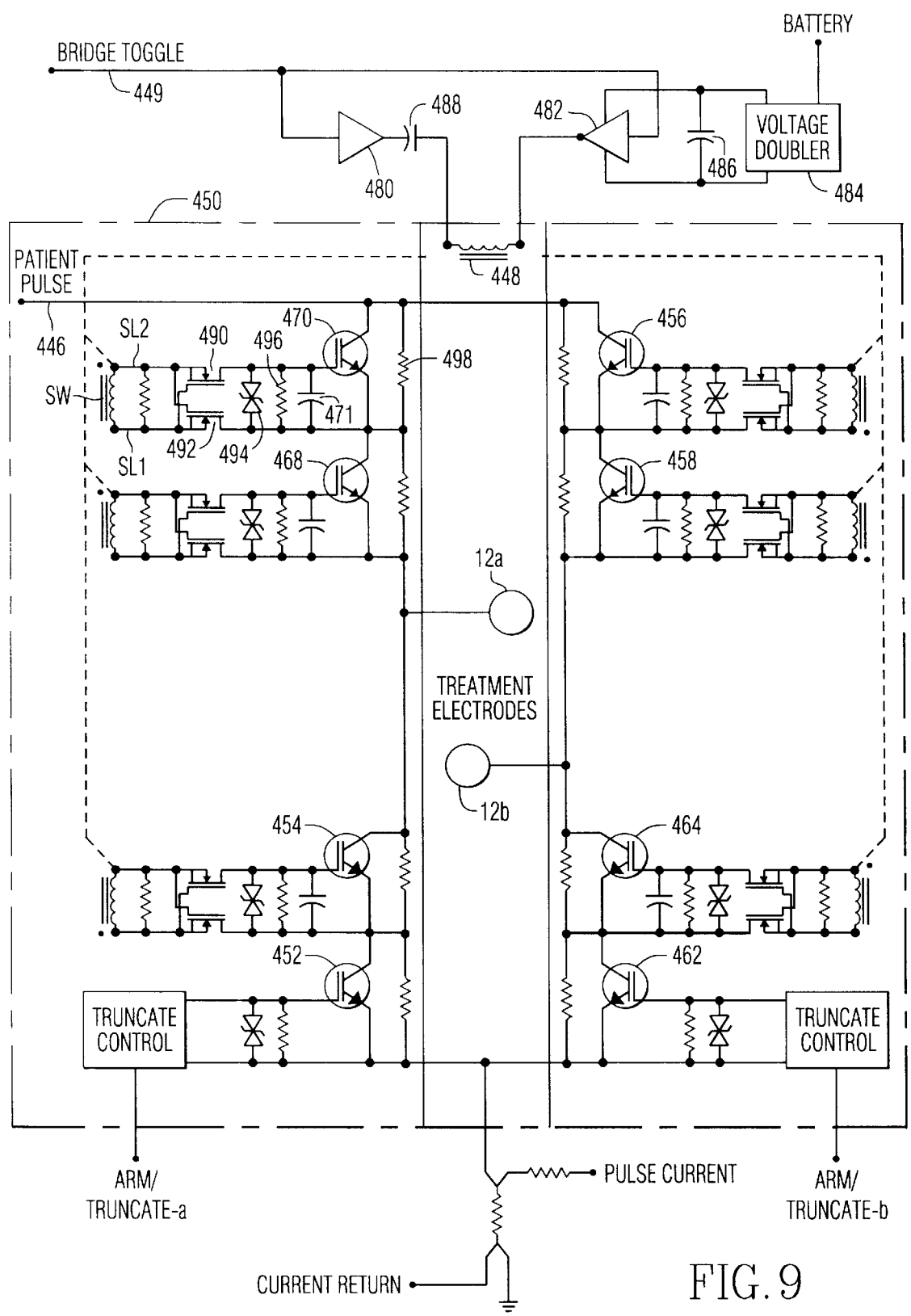

FIG. 7 illustrates one embodiment of a biphasic defibrillator circuit that can be used within defibrillator 22 in FIG. 2. Referring to FIG. 8, polarity reversal during delivery of the biphasic energy pulse can be accomplished by using an H-bridge having a plurality of IGBTs which can be triggered by a transformer 448 with multiple secondary windings SW, each having two legs with polarities SL1, SL2. The pulse delivery typically is disabled during the period when the H-bridge is reconfigured for polarity reversal because it is not desired that the H-bridge be switched while active, or "hot". In general, the proper H-bridge leg of the pulse delivery chain of semiconductor switches is turned on before the energy from the energy reservoir is switched to the bridge.

The biphasic defibrillation circuitry of FIG. 7 can be similar to the circuitry for the monophasic defibrillator in FIG. 5. Indeed, the charging circuitry for both the monophasic and biphasic devices can be the same. However, for a biphasic defibrillator, polarity reversal of the patient therapy pulse is effected by using an H-bridge circuit and a second bank of opto-switches for gating the pulse delivery SCRs for the second phase of the biphasic pulse.

In general, the operational sequence for the defibrillator of FIG. 7 and FIG. 8 can be as follows:

1. H-bridge 450 can be configured for the delivery of the desired first phase polarity and the IGBTs in that leg of the bridge can be turned on.

2. The selected first phase polarity of the pulse can be delivered by activating the first opto-trigger chain. Energy is typically allowed to flow for about 4 milliseconds.

3. After the first phase of the pulse is delivered, the pulse is truncated and then the energy flow is stopped for approximately 100 microseconds while H-bridge 450 is reconfigured for energy flow of an opposite polarity through the patient electrode 12a, 12b connections.

4. The second opto-trigger bank is fired, delivering the remaining energy to the patient.

Either leg of the H-bridge 450 may be selected as the first phase of the pulse depending upon which OPTO TRIGGER signal 424, 426 from controller 24 is activated. Thus allowing for either a positive or negative first phase. OPTO TRIGGER signals 424, 426 may be separate signals from the controller 24.

Assuming that it is desired for a positive-going first phase, IGBTs 452, 454, 456, 458 can be turned on. When OPTO TRIGGER line 426 is activated, opto-triacs 435–439 fire SCRs 440443 and triac 444 connecting capacitors 401–405 in series delivering the first phase of the pulse to the patient. Upon completion of the first phase, transistor 452 is turned off, in response to a first control signal ARM\TRUNCATE-a from controller 24, thereby truncating the pulse. At this time the other leg of H-bridge 450 is turned on, including IGBTs 462, 464, 468, 470. When the second bank of opto-triggers is activated by opto-trigger line 424, opto-triacs 430–434 fire, gating SCRs 440–443 and triac 444, thereby delivering the second negative-going phase of the pulse.

Upon completion of the second phase, IGBT 462 is turned off via a separate second ARM\TRUNCATE-b signal from controller 24, thereby truncating the pulse. H-bridge 450 can be toggled via BRIDGE TOGGLE line 449 from controller 24 (not shown in FIG. 2) between phases by pulsing the multi-secondary transformer, 448. The primary winding of transformer 448 is pulsed by amplifier 480 for positive going pulses and amplifier 482 for negative-going pulses. One of amplifiers 480, 482 is an inverter as shown in FIG. 8.

In general, amplifiers 480, 482 are MOSFET drivers that are able to deliver high peak currents, for example, 1 to 3 amperes, into capacitive loads for short periods. Typically, the output of amplifier 480 is opposite in polarity to the output of amplifier 482 at any given time. That is, when one is high, the other is low. Amplifier 482 can derive its input from voltage doubler device 484 which increases battery voltage to approximately 12 volts across capacitor 486. Capacitor 486 can be used as a power supply for amplifiers 480, 482.

Capacitor 488 typically is in series with the output of amplifiers 480, 482 and the primary of transformer 488 and performs a dual role. First, it can isolate the outputs of amplifiers 480, 482 from each other minimizing the likelihood of electrical shorting. Secondly, it also can charge to the level of the output of amplifiers 480, 482. During the switching transition for H-bridge 450 by amplifiers 480, 482, the charge voltage of capacitor 488 can be added to the transition voltage of amplifiers 480, 482 applying up to about 20 volts to the primary of transformer 448. The resulting pulse energy developed across the secondaries of transformer 448 gate the IGBTs 452, 454, 456 and 458 or alternatively, 462, 464, 468 and 470 in the H-bridge 450 turning them on or off as desired. This configuration can maintain the gate voltage on those IGBTs that are "on" for the required duration of the pulse phase.

This circuit transfers energy from low voltage circuit potential to the gate terminal of high voltage output transistors (454, 456, 458, 464, 468, 470) for turning them on for the length of the defibrillator pulse. Enough energy must be transferred from the primary of transformer 448 to the drive storage capacitor 471 of all the transistors attached to the multiple secondaries. This can be done with one transition of voltage across the primary and not multiple transitions or oscillations per phase of the defibrillator pulse.

Voltage doubler 484 doubles battery voltage and stores it on capacitor 486. BRIDGE TOGGLE line 449 is initially low and the outputs of transformer drivers 480 and 482 are high and low, respectively. This stores an initial voltage equal to the doubled battery voltage across capacitor 488. When BRIDGE TOGGLE line 449 goes high the outputs of transformer drivers 480 and 482 toggle states and combine with capacitor 488 to drive the primary of the transformer with twice the doubled battery voltage. This charges the non-dotted lines SL1 of the secondaries to approximately +4 times the battery voltage minus some losses. This also charges the dotted sides SL2 of the secondaries to approximately −4 times the battery voltage minus some losses.

This overall circuit configuration allows the necessary output transistors to be turned on or held off as required by the phase of the output defibrillator pulse. The primary transformer drive voltage is large enough so that the transformer can be easily wound of multi-filar magnet wire because a 1:1 turns ratio is adequate. High current output MOSFET drives for transformer drivers 480 and 482 drive the primary with a large fast rising current that helps to minimize the size of the required transformer toroid core.

The drive storage capacitor 471 must be large enough to support the gate drive requirements of the high voltage transistors for the maximum duration of a pulse (up to 50 mS). Both the positive and negative voltages are maintained for the length of the pulse. The off transistors require the negative gate voltage to resist the transient dV/dT drain-gate feedback currents that would try to turn these devices on and destroy them. The negative voltage ensures that they will remain off even after absorbing the feedback current.

The drive storage capacitor 471 charges positive by current flowing out of the dotted secondary SL2 of transformer 448, through the reverse parasitic diode 490, through capacitor 471, and through the on resistance 492 back to the opposite side of the secondary. After the energy in the transformer has been transferred, both 490 and 492 are held off because their gate terminals are shorted to their source terminals through the transformer secondary in steady state. This keeps the charge on capacitor 471. When BRIDGE TOGGLE line signal 449 is toggled, the current flow is reversed, 490 and 492 operating modes are complimentary and negative voltage is stored on capacitor 471. Bi-directional voltage clamp 494 limits both positive and negative excursions at the gates of the transistors. High value resistors 496, 498 dampen or prohibit small voltage oscillators due to parasitics. Although the charging methodology for insulated gate bipolar transistor 470 is described, it will be readily apparent to those skilled in the art that the components for IGBTS 468, 464, 462, 458, 456, 454 and 452 is identical.

There is one additional step that has to be done before actually closing the charge relay (220). The capacitor bank (201–205) has to be discharged in parallel for a short period of time to allow the capacitor voltage to balance. If a previous defibrillator pulse has been truncated, the capacitors may not have the same voltage on each one of them because they have slightly different values and therefore will discharge to slightly different voltage levels with the same series current flowing through them. If the voltage is not balanced, a very large current will flow when a charging switch (220, mechanical or electrical) is like connecting terminals of charged capacitors directly across each other, the higher voltage capacity will try to charge the lower voltage capacity through a very low impedance. The minimum time the capacitors need to discharge to balance is a function of the tolerances (or mismatch) of the capacitor values. This condition only applies to the method of charging in parallel/discharging in series along with a pulse truncation that does not dump all of the remaining energy on the energy storage capacities and leaves a certain amount of voltage present.

This method of discharging the capacitors in parallel is somewhat dependent on the charge current path device configuration since the same diode chains are used to direct the discharge current, but for different capacitors. The same capacitor does not use any of the same diodes for both charge and discharge current paths. Prior art parallel to series defibrillators generally waste all the remaining energy at the truncation time by high current internal "shorts" of the individual capacitors. This is a brute force method of shutting off the external pulse. They also teach using the terminal "shorts" to discharge the capacitor bank without delivering a pulse to the patient. The internal "shorts" require numerous large components for circuit survival and operation and they also contribute to energy losses in the outgoing defibrillator pulse. The method of the present invention of internal discharge for parallel-series capacitors is much smaller and more realizable with size constraints for a patient-worn defibrillator device.

While specific embodiments of practicing the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting to the scope of the invention which is to be given the full breadth of the following claims, and any and all embodiments thereof.

What is claimed is:

1. A patient-worn energy delivery apparatus for imparting electrical therapy to the body of a patient responsive to an occurrence of a treatable condition, the apparatus comprising:

a. a voltage converter for converting electrical energy from an initial voltage to a final voltage;

b. a defibrillator adapted to be electrically coupled between the converter and the patient, the defibrillator having an energy defibrillator producing precharged electrical pulses therefrom, the electrical pulses being one of a defibrillator pulse and cardioversion pulses;

c. an energy delivery controller adapted to be electrically coupled to the patient and the converter and the defibrillator, the controller causing the converter to provide the electrical energy to the defibrillator, the controller causing the defibrillator to apply a selectable portion of the electrical energy in the form of one of the defibrillator pulses and the cardioversion pulses to the body of the patient, responsive to the treatable condition;

d. means for sensing the voltage and current being applied to the body of the patient by the defibrillator;

e. timer for determining a time length of the electrical pulse being applied to the body of the patient; and f. means for terminating the electrical pulse being delivered to the body of the patient based on a product of the sensed voltage, current and the time length of the electrical pulse.

2. The apparatus of claim 1 wherein the precharged electrical pulses are biphasic exponential-shaped pulses.

3. The apparatus of claim 2 wherein each of the biphasic exponential pulses has a positive-going pulse segment and a negative-going pulse segment and said terminating means terminates the positive-going pulse based on a predetermined energy factor dependent on the sensed voltage and current and the time length and a remaining amount of the electrical energy is applied to the patient during the negative-going pulse segment.

4. The apparatus of claim 1, further comprising means for sensing an electrical impedance between the converter and the patient to determine an operating condition of the defibrillator.

5. The apparatus of claim 1 wherein the energy reservoir includes a plurality of capacitors, the plurality of capacitors being adapted to charge substantially in parallel and discharge substantially in series.

6. The apparatus of claim 5 wherein the preshaped electrical pulses are biphasic exponential pulses.

7. The apparatus of claim 6 wherein each of the biphasic exponential pulses has a positive-going pulse segment and a negative-going pulse segment and a selected amount of the electrical energy is applied to the patient during the positive-going pulse segment and a remaining amount of the electrical energy is applied to the patient during the negative-going pulse segment.

8. The apparatus of claim 7 further comprising a H-bridge to produce the positive-going pulse segment and the negative-going pulse segment of each of the biphasic exponential signals; said H-bridge being further comprised of:

a first plurality of insulated gate bipolar transistors having a first polarity;

a second plurality of insulated gate bipolar transistors having a second polarity;

a transformer having first and second secondary windings for selectively triggering said first and second plurality of insulated gate bipolar transistors;

means for delivering the positive-going pulse segment through said first plurality of insulated gate bipolar transistors; and means for delivering the negative-going pulse segment through said second plurality of insulated gate bipolar transistors.

9. The apparatus of claim 8 wherein the selected amount of electrical energy is about 60% and the remaining amount of electrical energy is about 40%.

10. The apparatus of claim 5 further comprising a plurality of silicon controller rectifiers and a plurality of opto-triacs, wherein selected ones of the plurality of capacitors are serially connected with selected others of the plurality of capacitors, respective ones of the plurality of silicon controlled rectifiers are serially interposed between adjacent ones of said selected ones and others, and each of the plurality of silicon controlled rectifiers being controllable with a respective one of the plurality of opto-triacs, the plurality of opto-triacs causing the silicon controlled rectifiers to conduct responsive to a therapy initiation command from the controller.

11. The apparatus of claim 1 further comprising a plurality of electrodes interposed between the defibrillator and the patient, the plurality of electrodes having a conductive surface adapted for placement adjacent the patient's skin and having an impedance reducing means contained therein for reducing the impedance between the plurality of electrodes and the patient's skin, the impedance reducing means being activated responsive to the occurrence of the treatable condition.

12. The apparatus of claim 11 further comprising:

a. a source of electrical energy at a first voltage; and b. a carrier means in the form of an upper body harness or garment to be worn by the patient, the carrier means holding the plurality of electrodes therein.

13. The apparatus of claim 1 wherein the defibrillator further comprises at least one insulated gate bipolar transistor for conducting the electrical energy through the patient responsive to the controller.

14. The apparatus of claim 1 wherein the voltage converter includes an inductive-boost voltage generator having a first stage having a first stage output voltage and a second stage having a second stage output voltage.

15. The apparatus of claim 14 wherein the first stage output voltage is regulated independently of the second stage output voltage.

16. The apparatus of claim 15 wherein the selectable portion is further determined by the controller using a minimum energy delivery period and a maximum energy delivery period.

17. The apparatus of claim 14 wherein at least one of the controller and the converter is shut down responsive to an overvoltage condition in at least one of the first stage voltage output and the second stage voltage output.

18. A patient-worn energy delivery apparatus for imparting electrical therapy to the body of a patient responsive to an occurrence of a treatable condition, the apparatus comprising:

a. a voltage converter converting electrical energy from an initial voltage to a final voltage at a plurality of charging rates, the converter including an inductive-boost generator;

b. a defibrillator electrically coupled between the converter and the patient, the defibrillator having a plurality of capacitors being adapted to charge substantially in parallel and discharge substantially in series and the defibrillator producing preshaped electrical pulses, the electrical pulses being approximately exponentially-shaped pulses and the electrical pulses being one of defibrillation pulses and cardioversion pulses;

c. an energy delivery controller electrically coupled to the patient and the converter and the defibrillator, the controller causing the converter to provide the electrical energy to the defibrillator, the controller causing the defibrillator to apply a selectable portion of the electrical energy in the form of one of the defibrillation pulses and the cardioversion pulses to the body of the patient responsive to the occurrence of the treatable condition, the selectable portion being determined by a voltage across selected ones of the plurality of capacitors and a pulse current;

d. means for sensing the voltage and current being applied to the body of the patient by the defibrillator;

e. timer for determining a time length of the electrical pulse being applied to the body of the patient; and f. means for terminating the electrical pulse being delivered to the body of the patient based on a product of the sensed voltage, current and the time length of the electrical pulse.

19. The apparatus of claim 18 wherein the controller causing the converter to provide the electrical energy to the defibrillator at selected ones of the plurality of charging rates.

20. The apparatus of claim 18 wherein the preshaped electrical pulses are biphasic exponential pulses, and each of the biphasic exponential pulses has a positive-going pulse segment and a negative-going pulse segment, a selected amount of the electrical energy being applied to the patient during the positive-going pulse segment and a remaining amount of the electrical energy being applied to the patient during the negative-going pulse segment.

21. The apparatus of claim 20 further comprising a H-bridge to produce the positive-going pulse segment and the negative-going pulse segment of each of the biphasic exponential signals.

22. The apparatus of claim 18 wherein the defibrillator further comprises a plurality of silicon controlled rectifiers and a plurality of opto-triacs and at least one insulated gate bipolar transistor, wherein selected ones of the plurality of capacitors are serially connected with selected others of the plurality of capacitors, respective ones of the plurality of silicon controlled rectifiers are serially interposed between adjacent ones of said selected ones and others, and each of the plurality of silicon controlled rectifiers being controllable with a respective one of the plurality of opto-triacs, the plurality of opto-triacs causing the silicon controlled rectifiers to conduct and the at least one insulated gate bipolar transistor conducting the electrical energy through the patient responsive to a therapy initiation command from the controller.

23. The apparatus of claim 18 further comprising:

a. a plurality of electrodes interposed between the defibrillator and the patient, the plurality of electrodes having a conductive surface adapted for placement adjacent the patient's skin and having an impedance reducing means contained therein for reducing the impedance between the plurality of electrodes and the patient's skin, the impedance reducing means being activated responsive to the occurrence of the treatable condition;

b. a source of electrical energy at a first voltage; and c. a carrier means in the form of an upper body harness or garment to be worn by the patient, the carrier means holding the plurality of electrodes therein.

24. The apparatus of claim 23 wherein the defibrillator further comprises at least one insulated gate bipolar transistor for conducting the electrical energy through the patient responsive to the controller.

* * * * *